United States Patent [19]

Jones et al.

[11] 4,165,377
[45] Aug. 21, 1979

[54] GUANIDINO IMIDAZOLES AND THIAZOLES

[75] Inventors: Derrick F. Jones, Wilmington, Del.; Tobias O. Yellin, Wallingford, Pa.

[73] Assignee: ICI Americas Inc., Wilmington, Del.

[21] Appl. No.: 897,910

[22] Filed: Apr. 19, 1978

[30] Foreign Application Priority Data

Apr. 20, 1977 [GB] United Kingdom ............... 16389/77

[51] Int. Cl.$^2$ .................. C07D 277/38; C07D 233/88; A61K 31/425; A61K 31/415
[52] U.S. Cl. .............................. 424/270; 260/306.8 R; 260/326 A; 260/326 N; 424/273; 542/417; 542/418; 542/420; 548/337
[58] Field of Search .................. 260/306.8 R; 542/420, 542/418, 417; 548/337; 424/270, 273

[56] References Cited

U.S. PATENT DOCUMENTS

| | | | |
|---|---|---|---|
| 3,876,647 | 4/1975 | Durant et al. | 424/263 |
| 3,897,444 | 7/1975 | Durant et al. | 260/306.8 R |
| 3,905,984 | 9/1975 | Durant et al. | 260/294.8 H |
| 3,920,822 | 11/1975 | Durant et al. | 424/263 |
| 3,932,427 | 1/1976 | Durant et al. | 260/295 E |
| 3,950,333 | 4/1976 | Durant et al. | 260/302 A |
| 3,950,353 | 4/1976 | Durant et al. | 260/307 R |
| 3,975,530 | 8/1976 | Durant et al. | 424/270 |
| 4,018,391 | 4/1977 | Durant et al. | 424/269 |
| 4,018,928 | 4/1977 | Durant et al. | 424/263 |
| 4,018,931 | 4/1977 | Durant | 424/269 |
| 4,022,797 | 5/1977 | Durant et al. | 260/302 R |
| 4,038,408 | 7/1977 | Durant et al. | 424/220 |
| 4,049,672 | 9/1977 | Durant et al. | 548/342 |
| 4,053,473 | 10/1977 | Durant et al. | 548/342 |
| 4,062,863 | 12/1977 | Ganellin | 260/306.8 R |

FOREIGN PATENT DOCUMENTS

| | | |
|---|---|---|
| 843814 | 1/1976 | Belgium. |
| 832660 | 2/1976 | Belgium. |
| 832661 | 2/1976 | Belgium. |
| 832662 | 2/1976 | Belgium. |
| 832663 | 2/1976 | Belgium. |
| 832664 | 2/1976 | Belgium. |
| 832665 | 2/1976 | Belgium. |
| 841526 | 11/1976 | Belgium. |
| 843839 | 1/1977 | Belgium. |
| 843840 | 1/1977 | Belgium. |
| 844503 | 1/1977 | Belgium. |
| 844504 | 1/1977 | Belgium. |
| 846452 | 3/1977 | Belgium. |
| 2604056 | 5/1976 | Fed. Rep. of Germany. |
| 1296544 | 11/1972 | United Kingdom. |
| 1305546 | 2/1973 | United Kingdom. |
| 1305547 | 2/1973 | United Kingdom. |
| 1305548 | 2/1973 | United Kingdom. |
| 1305549 | 2/1973 | United Kingdom. |
| 1305550 | 2/1973 | United Kingdom. |
| 1307539 | 2/1973 | United Kingdom. |
| 1338169 | 11/1973 | United Kingdom. |
| 1341375 | 12/1973 | United Kingdom. |
| 1341376 | 12/1973 | United Kingdom. |
| 1395929 | 5/1975 | United Kingdom. |
| 1397436 | 6/1975 | United Kingdom. |
| 1398426 | 6/1975 | United Kingdom. |
| 1399283 | 6/1975 | United Kingdom. |
| 1400319 | 7/1975 | United Kingdom. |
| 1419994 | 1/1976 | United Kingdom. |
| 1421792 | 1/1976 | United Kingdom. |
| 1421999 | 1/1976 | United Kingdom. |
| 1422408 | 2/1976 | United Kingdom. |
| 1431589 | 4/1976 | United Kingdom. |
| 1343931 | 11/1977 | United Kingdom. |
| 1493931 | 11/1977 | United Kingdom. |
| 1496787 | 5/1978 | United Kingdom. |
| 1497260 | 5/1978 | United Kingdom. |

Primary Examiner—Mark L. Berch

[57] ABSTRACT

The invention relates to guanidine derivatives of imidazoles and thiazoles which are histamine H-2 antagonists and which inhibit the secretion of gastric acid, to methods for their manufacture, to pharmaceutical compositions containing them and to methods of using such guanidine derivatives and compositions. The guanidine derivatives are of the general formula I:

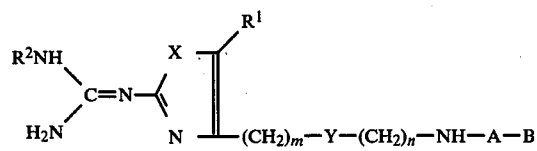

in which X is S or NH, Y is CH$_2$, a direct bond or a vinylene radical, m is 0 to 4 and n is 1 to 4, R$^1$ is hydrogen, halogen or alkyl, R$^2$ is hydrogen, alkyl, alkanoyl or aroyl, A is a 3,4-dioxocyclobuten-1,2-diyl radical or C=Z in which Z is O, S, NCN, NNO$_2$, CHNO$_2$, NCONH$_2$, C(CN)$_2$, NCOR$^3$, NCO$_2$R$^3$, NSO$_2$R$^3$ or NR$^4$ in which R$^3$ is alkyl or aryl and R$^4$ is hydrogen or alkyl, B is alkoxy or alkylthio or NR$^5$R$^6$ in which R$^5$ and R$^6$ are independently hydrogen, alkyl, alkenyl, cycloalkyl, hydroxyalkyl, alkoxyalkyl, alkylaminoalkyl or dialkylaminoalkyl; and the salts thereof.

20 Claims, No Drawings

GUANIDINO IMIDAZOLES AND THIAZOLES

This invention relates to guanidine derivatives which are histamine H-2 antagonists and which inhibit gastric acid secretion.

It is postulated that the physiologically active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.*, 1966, 27, 427) and the action of histamine at this receptor is blocked (antagonized) by classical "antihistamine" drugs such as mepyramine (pyrilamine). The second histamine receptor has been named the H-2 receptor (Black et al., Nature, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

In U.K. Pat. Nos. 1,338,169 and 1,397,436 there are described histamine H-2 receptor antagonists which are imidazole and thiazole derivatives having a side chain in the 4-position, to the end of which is attached, for example, a urea, thiourea, guanidine or N-cyanoguanidine. It has now been discovered that if an optionally-substituted guanidino radical is inserted in the 2-position of such compounds, there are produced compounds which are potent histamine H-2 receptor antagonists.

According to the invention there is provided a guanidine derivative of the formula I:

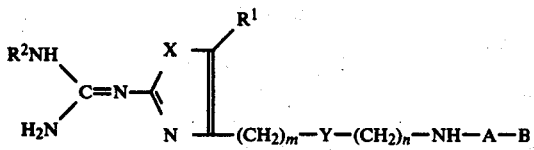

in which X is a sulphur atom or an NH radical; Y is a direct bond, a methylene radical or a cis- or trans-vinylene radical; m is 0 to 4 and n is 1 to 4; $R^1$ is a hydrogen or halogen atom or an alkyl radical of 1 to 6 carbon atoms; $R^2$ is a hydrogen atom, an alkyl radical of 1 to 10 carbon atoms, an alkanoyl radical of 1 to 6 carbon atoms or an aroyl radical of 7 to 11 carbon atoms; A is a 3,4-dioxocyclobuten-1,2-diyl radical or a radical of the formula C=Z in which Z is an oxygen or sulphur atom or a radical of the formula NCN, NNO$_2$, CHNO$_2$, NCONH$_2$, C(CN)$_2$, NCOR$^3$, NCO$_2$R$^3$, NSO$_2$R$^3$ or NR$^4$ in which $R^3$ is an alkyl radical of 1 to 6 carbon atoms or an aryl radical of 6 to 12 carbon atoms and $R^4$ is a hydrogen atom or an alkyl radical of 1 to 6 carbon atoms; B is an alkoxy or alkylthio radical of 1 to 6 carbon atoms or a radical of the formula NR$^5$R$^6$ in which $R^5$ and $R^6$, which may be the same or different, are hydrogen atoms, alkyl radicals of 1 to 10 carbon atoms, alkenyl radicals of 3 to 10 carbon atoms in which the double bond is separated from the nitrogen atom of NR$^5$R$^6$ by at least one carbon atom, cycloalkyl radicals of 3 to 8 carbon atoms (primary hydroxy)alkyl radicals of 2 to 6 carbon atoms in which the oxygen atom is separated from the nitrogen atom of NR$^5$R$^6$ by at least two carbon atoms, alkoxyalkyl radicals of 3 to 10 carbon atoms in which the oxygen atom is separated from the nitrogen atom of NR$^5$R$^6$ by at least two carbon atoms, alkylaminoalkyl radicals of 3 to 10 carbon atoms in which the nitrogen atom is separated from the nitrogen atom of NR$^5$R$^6$ by at least two carbon atoms; or dialkylaminoalkyl radicals of 4 to 10 carbon atoms in which the nitrogen atom is separated from the nitrogen atom of NR$^5$R$^6$ by at least two carbon atoms; and the pharmaceutically acceptable acid-addition salts thereof.

It is to be understood that, in the above formula I and throughout this specification, although the double bonds in both side chains have been inserted in particular positions, various other tautomeric forms are possible, and this invention includes such tautomeric forms within this scope, both in terms of the compound of the invention and in terms of the manufacturing processes.

The term "halogen" as used herein means that recognized group of halogens which have an atomic weight of at most 127 and are chlorine, fluorine, bromine and iodine.

A particular value for $R^1$ when it is a halogen atom or an alkyl radical is a bromine atom or a methyl radical.

A particular value for $R^2$ when it is an alkyl, alkanoyl or aroyl radical is a methyl, n-butyl, acetyl, propionyl or benzoyl radical.

A particular value for $R^3$ is a methyl or p-tolyl radical.

A particular value for $R^4$ is a methyl radical.

A particular value for B when it is an alkoxy or alkylthio radical is a methoxy, ethoxy or methylthio radical.

A particular value for $R^5$ or $R^6$ when it is an alkyl, alkenyl, cycloalkyl, (primary hydroxy)alkyl, alkoxyalkyl or dialkylaminoalkyl radical is a methyl, ethyl, n-propyl, isopropyl, n-hexyl, allyl, cyclohexyl, 2-hydroxyethyl, 3-hydroxypropyl, 2-methoxyethyl or 2-dimethylaminoethyl radical.

The following are 8 preferred features of the guanidine derivative of the formula I. When any one of these 8 features is taken, either singly or in combination, with the other general features of the guanidine derivatives of the formula I listed above, there are obtained preferred sub-groups of compounds within the above general definition.

1. X is a sulphur atom.
2. $R^1$ is a hydrogen atom.
3. $R^2$ is a hydrogen atom or an alkyl radical of 1 to 6 carbon atoms.
4. B is a radical of the formula NR$^5$R$^6$ in which $R^6$ is a hydrogen atom.
5. B is an alkoxy radical of 1 to 4 carbon atoms or an alkylthio radical of 1 to 4 carbon atoms.
6. A is a 3,4-dioxocyclobuten-1,2-diyl radical or a radical of the formula C=Z in which Z is an oxygen or sulphur atom or a radical of the formula NCN, NNO$_2$ or CHNO$_2$.
7. Y is a direct bond and m is 2 and n is 2.
8. B is a radical of the formula NR$^5$R$^6$ in which $R^5$ is a methyl radical and $R^6$ is a hydrogen atom.

The following group of compounds is particularly preferred:
2-guanidino-4-[4-(2-cyano-3-methylguanidino)butyl]-thiazole;
2-(2-methylguanidino)-4-[4-(2-cyano-3-methyl-guanidino)butyl]thiazole;
2-guanidino-4-[4-(3-cyano-2-methylisoureido)butyl]-thiazole;

1-[4-(2-guanidinothiazol-4-yl)butylamino]-1-methylamino-2-nitroethylene;
2-guanidino-4-[4-(2-nitroguanidino)butyl]thiazole;
1-[4-(2-guanidinothiazol-4-yl)butylamino]-2-methylaminocyclobutene-3,4-dione;

and the pharmaceutically acceptable acid-addition salts thereof.

A suitable pharmaceutically acceptable acid-addition salt of the guanidine derivative of the invention is, for example, a salt formed with hydrochloric, hydrobromic, phosphoric, sulphuric, acetic, citric or maleic acid.

All of the compounds within the scope of the present invention can be prepared in accordance with the principles, processes and techniques illustrated in the following described processes and Examples. In the following described processes X, Y, m, n, A, B, $R^1$, $R^2$, $R^3$, $R^4$, $R^5$ and $R^6$ have the meanings stated above unless indicated otherwise.

The processes that can be used to prepare the compounds of this invention are as follows:

(a) reaction of a compound of the formula II:

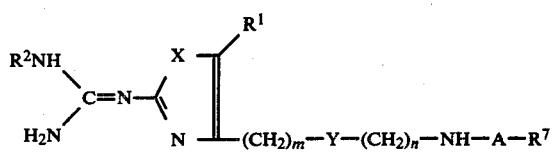

in which $R^7$ is a displaceable radical, with a compound of the formula B-H;

(b) for those compounds in which A is a radical of the formula C=Z in which Z is a sulphur or oxygen atom and B is a radical of the formula $NR^5R^6$ in which $R^6$ is a hydrogen atom and $R^5$ has the value stated above other than a hydroxyalkyl or alkylaminoalkyl radical, reaction of a compound of the formula III:

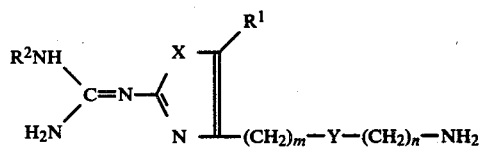

with a compound of the formula $R^8N=C=D$ in which D is an oxygen or sulphur atom and $R^8$ is a hydrogen atom or an alkyl, alkenyl, cycloalkyl, alkoxyalkyl or dialkylaminoalkyl radical such as suitably methyl, ethyl, n-propyl, isopropyl, n-hexyl, allyl, cyclohexyl, 2-methoxyethyl or dimethylaminoethyl, depending on the identity of $R^5$ desired;

(c) for those compounds in which A is a radical of the formula C=Z in which Z is a radical of the formula NCN and B is a radical of the formula $NR^5R^6$ in which $R^5$ and $R^6$ are hydrogen atoms, reaction of a compound of the formula III with dicyanimide or a salt thereof;

(d) reaction of a compound of the formula III with a compound of the formula IV:

$$R^7-A-B \qquad IV$$

in which $R^7$ is a displaceable radical;

(e) for those compounds in which $R^2$ is a hydrogen atom or an alkyl radical, A is a radical of the formula C=Z in which Z is a radical of the formula $NCONH_2$ and B is a radical of the formula $NR^5R^6$, hydrolysis of a compound of the formula I in which $R^2$ is a hydrogen atom or an alkyl radical, A is a radical of the formula C=Z in which Z is a radical of the formula NCN and B is a radical of the formula $NR^5R^6$;

(f) for those compounds in which $R^2$ is an alkanoyl or aroyl radical, reaction of a compound of the formula I in which $R^2$ is a hydrogen atom with an acid, or an acylating agent derived from an acid, of the formula $R^9CO_2H$ in which $R^9$ is a hydrogen atom, an alkyl radical of 1 to 9 carbon atoms or an aryl radical of 6 to 10 carbon atoms;

(g) for those compounds in which $R^2$ is a hydrogen atom or an alkyl radical and B is a radical of the formula $NR^5R^6$, hydrolysis of a compound of the formula V:

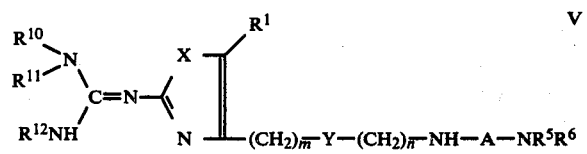

in which $R^{10}$ is a hydrogen atom or an alkyl radical of 1 to 10 carbon atoms, one of $R^{11}$ and $R^{12}$ is an alkanoyl radical of 1 to 6 carbon atoms or an aroyl radical of 7 to 11 carbon atoms and the other is a hydrogen atom;

(h) for those compounds in which A is a radical of the formula C=Z in which Z is an oxygen atom and B is a radical of the formula $NR^5R^6$, hydrolysis of a compound of the formula VI:

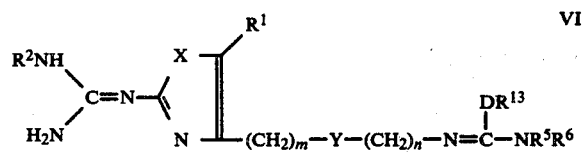

in which D is an oxygen or sulphur atom and $R^{13}$ is an alkyl radical of 1 to 6 carbon atoms;

(i) for those compounds in which A is a radical of the formula C=Z in which Z is a radical of the formula $NR^4$ and B is an alkoxy or alkylthio radical of 1 to 6 carbon atoms, alkylation of a compound of the formula VII:

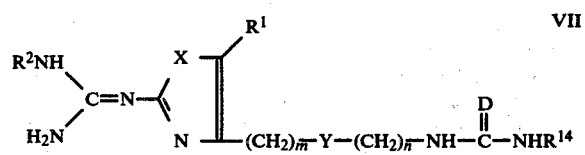

in which D is an oxygen or sulphur atom and $R^{14}$ is a hydrogen atom or an alkyl radical of 1 to 6 carbon atoms;

(j) for those compounds in which B is a radical of the formula $NR^5R^6$ in which at least one of $R^5$ and $R^6$ is other than a hydrogen atom, reaction of a compound of the formula VIII:

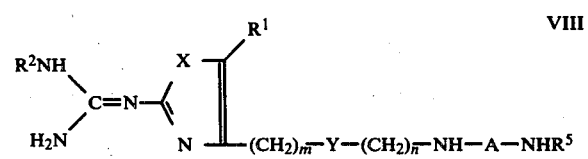

with an alkylating agent derived from $R^{15}$-H in which $R^{15}$ is an alkyl, alkenyl, cycloalkyl, hydroxyalkyl, alkoxyalkyl, alkylaminoalkyl or dialkylaminoalkyl radical such as suitably methyl, ethyl, n-propyl, isopropyl, n-hexyl, hydroxypropyl, allyl, cyclohexyl, 2-methoxyethyl, 2-dimethylaminoethyl or ethylaminoethyl, depending on the identity of B desired;

(k) for those compounds in which A is a radical of the formula C=Z in which Z is a radical of the formula NCN, $NCOR^3$, $NCO_2R^3$ or $NSO_2R^3$ and B is a radical of the formula $NR^5R^6$, reaction of a compound of the formula IX:

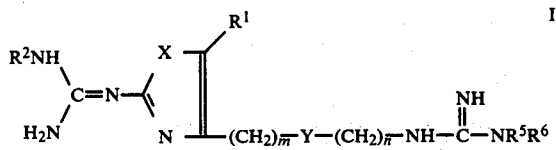

with a compound of the formula $R^7CN$, $R^7COR^3$, $R^7CO_2R^3$ or $R^7SO_2R^3$ in which $R^7$ is a displaceable atom or radical;

(l) for those compounds in which A is a radical of the formula C=Z in which Z is a radical of the formula NCN, $NCOR^3$, $NCO_2R^3$ or $NSO_2R^3$, and B is a radical of the formula $NR^5R^6$ in which $R^6$ is a hydrogen atom, reaction of a compound of the formula X:

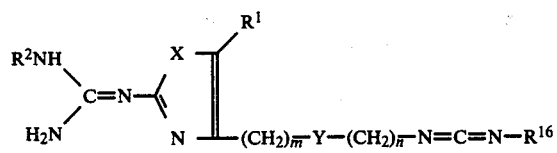

in which $R^{16}$ is either a radical of the formula $R^5$ or a radical of the formula CN, $COR^3$, $CO_2R^3$ or $SO_2R^3$, with a compound of the formula $H_2N$—$R^{17}$ in which $R^{17}$ is either a radical of the formula CN, $COR^3$, $CO_2R^3$ or $SO_2R^3$, or a radical of the formula $R^5$ respectively;

(m) for those compounds in which A is a radical of the formula C=Z in which Z is a radical of the formula NCN, $NCOR^3$, $NCO_2R^3$ or $NSO_2R^3$ and B is a radical of the formula $NR^5R^6$ in which $R^6$ is a hydrogen atom, reaction of a compound of the formula III with a compound of the formula XI:

$$R^5N=C=N-R^{18} \qquad XI$$

in which $R^{18}$ is a radical of the formula CN, $COR^3$, $CO_2R^3$ or $SO_2R^3$;

(n) for those compounds in which A is a radical of the formula C=Z in which Z is a radical of the formula NCN, $NCONH_2$, $NCOR^3$, $NCO_2R^3$, $NSO_2R^3$ or $NR^4$ and B is a radical of the formula $NR^5R^6$, reaction of a compound of the formula XII:

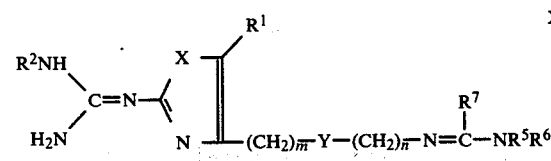

in which $R^7$ is a displaceable radical with a compound of the formula $H_2NCN$, $H_2NCONH_2$, $H_2NCOR^3$, $H_2NCO_2R^3$, $H_2NSO_2R^3$, or $H_2NR^4$;

(o) for those compounds in which A is a radical of the formula C=Z in which Z is a radical of the formula NCN, $NCOR^3$ $NCO_2R^3$ or $NSO_2R^3$, and B is a radical of the formula $NR^5R^6$, reaction of a compound of the formula XIII:

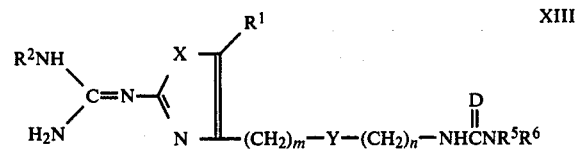

in which D is a sulphur or oxygen atom with a compound of the formula $H_2NCN$, $H_2NCOR^3$, $H_2NCO_2R^3$ or $H_2NSO_2R^3$; or (p) for those compounds in which B is a radical of the formula $NR^5R^6$, reaction of a molecule of the formula XIV:

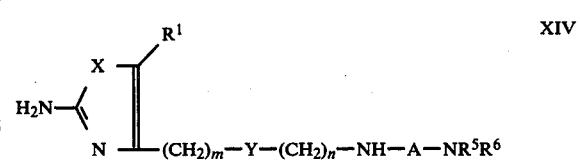

with a molecule of the formula XV:

in which $R^7$ is a displaceable radical.

When the process of the invention manufactures the compound of the formula I in the form of the free base and an acid-addition salt is required, the compound of the formula I in the free base form is reacted with an acid which affords a pharmaceutically acceptable anion.

Process (a) described above may be carried out using an excess of B-H, that is using an excess of the amine $R^5R^6NH$, optionally in the presence of a diluent or solvent such as water, methanol, ethanol and pyridine, or using an excess of the alcohol $R^{13}OH$ or the thiol $R^{13}SH$ in which $R^{13}$ is an alkyl radical of 1 to 6 carbon atoms, preferably in the form of a salt such as the sodium salt in the same alcohol or thiol as diluent or solvent. In process (a) $R^7$ is preferably an alkoxy or alkylthio radical, for example the methoxy, ethoxy or methylthio radical, or an amino radical. The process may be accelerated or completed by the application of heat, for example by boiling the reaction mixture.

Process (b) described above may be carried out using an excess of the isocyanate or isothiocyanate $R^8N=C=D$. When D is a sulphur atom, the reaction is preferably carried out in a diluent or solvent such as methanol or ethanol. When D is an oxygen atom, a non-alcoholic diluent or solvent must be used.

Process (c) described above may be carried out using the sodium salt of dicyanimide in a diluent or solvent such as n-butanol. The reaction may be accelerated or completed by the application of heat, for example by heating to the boiling point of the reaction mixture.

Process (d) described above may be carried out using an excess of the compound of the formula IV in a diluent or solvent such as methanol, ethanol or acetonitrile.

In process (d) R⁷ is preferably an alkoxy or alkylthio radical, for example a methoxy, ethoxy or methylthio radical. The reaction may be accelerated or completed by the application of heat, for example by heating to the boiling point of the reaction mixture.

Process (e) described above may be carried out using a dilute mineral acid, for example dilute hydrochloric acid, in a diluent or solvent such as water. The reaction may be accelerated or completed by application of heat, for example by heating to the boiling point of the reaction mixture.

Process (f) described above may be carried out in an inert diluent or solvent, and in the presence of a base, at or below room temperature. The diluent or solvent is preferably pyridine which also acts as the base. The reaction is preferably carried out using the acid chloride or the acid anhydride as the acylating agent.

In process (g) described above R¹¹ or R¹² is preferably an acetyl, propionyl or benzoyl radical. The process may be carried out using a dilute base such as sodium hydroxide in a diluent or solvent such as aqueous methanol or aqueous ethanol.

Process (h) described above may be carried out using a mild aqueous base, for example aqueous sodium carbonate. The reaction may be accelerated or completed by the application of heat, for example by heating to 100° C.

In process (i) described above, when D is a sulphur atom the reaction is preferably carried out using an alkyl ($C_1$ to $C_4$) halide, for example methyl iodide in a diluent or solvent such as ethanol. The reaction may be accelerated or completed by the application of heat.

In process (j) described above the alkylating agent derived from R¹⁵—H is preferably the corresponding halide such as methyl iodide.

In process (k) described above the displaceable atom is preferably a halogen atom.

In process (n) described above R⁷ is preferably a halogen atom or an alkoxy or alkylthio radical containing 1 to 4 carbon atoms.

In process (p) described above R⁷ is preferably an alkoxy or alkylthio radical containing 1 to 4 carbon atoms.

When Y is a direct bond, a methylene radical or a cis- or trans-vinylene radical, the starting material of the formula III for use in processes (b), (c) or (d) may be prepared by reaction of a compound of the formula XVI:

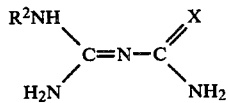

with a bromoketone of the formula XVII:

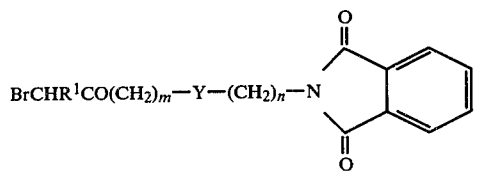

followed by hydrolysis of the phthalimido residue, for example as set out in following Examples 1, 5 or 17. When Y is a cis- or trans-vinylene radical, the starting material of the formula XVII may be prepared by a Wittig reaction, for example by reaction of a compound of the formula BrCHR¹CO(CH₂)ₘCH=P(Ph)₃ with an aldehyde of the formula XVIII:

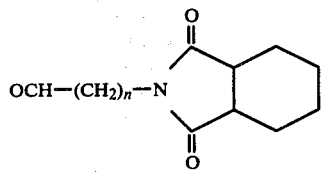

for example as set out in Examples 27 or 29 followed if necessary by isomerization of the double bond.

The starting material of the formula III in which R¹ is a halogen atom may be prepared by halogenation of the compound of the formula III in which R¹ is a hydrogen atom, for example as set out in Example 24.

The starting material of the formula II for use in process (a) may be prepared by reaction of a compound of the formula III with a compound of the formula R⁷—A—R⁷, such as dimethyl (cyanoimido)dithiocarbonate, in which R⁷ is a displaceable radical such as methoxy or methylthio, for example as set out in following Examples 1, 5, 7, 11, 12, 18, 19, 22, 27 or 29.

The starting material of the formula VI for use in process (h) may be obtained by alkylation of the compound of the formula I in which A is a radical of the formula C=Z in which Z is an oxygen or sulphur atom.

The starting material of the formula X for use in process (1) may be prepared, for example, by reaction of a compound of the formula XIX:

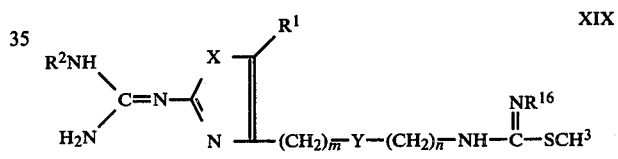

where R¹⁶ is a radical as described above under process (1); with silver nitrate.

When X is a sulphur atom the starting material for making compounds of formula XIV for use in process (p) may be prepared in the same way as for the starting material of the formula III, but using thiourea in place of the compound of the formula XVI. One of the processes of the present invention is then performed on the product, for example in processes (b), (c) and (d), the 2-aminothiazole derivative corresponding to the compound of the formula III, to give the compound of the formula XIV. When X is an NH radical, the starting material of the formula XIV may be prepared by reaction of cyanamide with an aminoketone of the formula XX:

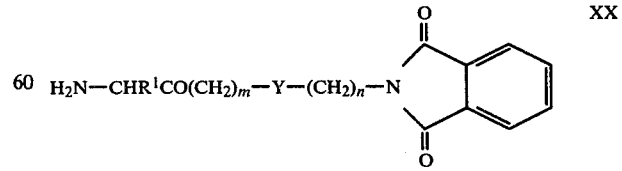

followed by removal of the phthalimido residue and elaboration of the side chain in the product, the 2-aminoimidazole derivative corresponding to the compound of the formula III.

The following examples will further serve to illustrate the present invention.

EXAMPLE 1

To a stirred mixture of 2-guanidino-4-(4-aminobutyl)-thiazole hydrochloride hydrobromide (0.4 g.) in ethanol (25 ml.) at ambient temperature was added triethylamine (0.3 ml.) and then dimethyl (cyanoimido)dithiocarbonate (0.18 g.) and the whole mixture stirred at room temperature for 5 hours. A solution of 33% w/v methylamine in ethanol (30 ml.) was then added and the mixture allowed to stand for 16 hours. A small amount of charcoal was added, the mixture stirred for a few minutes, and then filtered and the filtrate evaporated to dryness. The residual gum was purified by column chromatography on silica gel using chloroform/methanol/ammonia (s.g. 0.880) 80:20:0.5 v/v/v as eluant. The purified product (0.25 g.) was recrystallized from acetonitrile to give 2-guanidino-4-[4-(2-cyano-3-methylguanidino)butyl]thiazole, m.p. 165°–167.5° C.

The 2-guanidino-4-(4-aminobutyl)thiazole hydrochloride hydrobromide used at starting material may be prepared as follows:

A mixture of N-(6-bromo-5-oxohexyl)phthalimide (4.5 g.) and amidinothiourea (1.65 g.) in ethanol (300 ml.) was heated under reflux for 1 hour. The reaction mixture was allowed to cool and the product, 2-guanidino-4-(4-phthalimidobutyl)thiazole hydrobromide (4.3 g.), m.p. 218°–221° C., was filtered off.

A mixture of 2-guanidino-4-(4-phthalimidobutyl)-thiazole hydrobromide (3.43 g.) and potassium hydroxide (1.68 g.) in water (50 ml.) was heated at 100° C. for 15 minutes. The reaction mixture was then acidified to pH 2 with 2 N HCl, and the mixture heated at 100° C. for 1 hour. The cooled reaction mixture was extracted three times with ethyl acetate, the aqueous layer was evaporated to dryness and to the residue was added toluene which was evaporated to dryness. The resulting gummy solid was dissolved in methanol, the insoluble material filtered off and the filtrate evaporated to dryness to give 2-guanidino-4-(4-aminobutyl)thiazole hydrobromide hydrochloride. The free base (1.2 g.) was obtained by passage down an ion-exchange column [Amberlite IRA-400 (OH)] in 50% v/v methanol/water.

EXAMPLE 2

2-Guanidino-4-[2-(2-carbamoyl-3-methylguanidino)butyl]thiazole may be prepared by the following process:

A mixture of 2-guanidino-4-[4-(2-cyano-3-methylguanidino)butyl]thiazole (1.0 g.) and 2.5 N hydrochloric acid (12 ml.) is heated for four minutes on a steam bath. The precipitate formed on cooling is collected and applied to Merck 60 F-254 preparative thin layer chromatography plates and eluted with chloroform/methanol/ammonia (s.g. 0.880) 7:3:0.5 v/v/v. The desired product may then be obtained by extraction of the appropriate region of the developed chromatograms with ethanol.

EXAMPLE 3

A mixture of 2-guanidino-4-(4-aminobutyl)thiazole (0.213 g.) and methyl isothiocyanate (0.076 g.) in ethanol (5 ml.) was stirred at ambient temperature for 2 hours. The product, 2-guanidino-4-[4-(3-methylthioureido)butyl]thiazole (0.2 g.), was filtered off and dried, m.p. 189°–192° C.

EXAMPLE 4

2-Guanidino-4-[2-(3-methylureido)butyl]thiazole may be prepared by the following process:

A solution of 2-guanidino-4-[4-(3-methylthioureido)butyl]thiazole in ethanol (15 ml.) is treated with the appropriate amount of maleic acid to give a solution containing 0.42 g. of the hydrogen maleate salt. This solution is treated with methyl iodide (0.17 g.) and the mixture heated under reflux for 1.5 hours. Concentration of the reaction mixture to 5 ml. and collection of the precipitated solid gives 2-guanidino-4-[2-(2,3-dimethylisothioureido)butyl]thiazole hydrogen maleate hydriodide.

A solution of 2-guanidino-4-[2-(2,3-dimethylisothioureido)butyl]thiazole hydrogen maleate hydriodide (0.8 g.) in water (10 ml.) is treated with an aqueous solution of potassium carbonate (0.3 g. in 5 ml. water) and the solution heated on a steam bath for four hours. After allowing to stand at room temperature for 16 hours the aqueous layer is decanted from the brown gum and the brown gum applied to Merck 60 F-254 preparative thin layer chromatography plates and eluted with chloroform/methanol/ammonia (s.g. 0.880) 5:1:0.1 v/v/v. The desired product may then be obtained by extraction of the appropriate region of the chromatograms with ethanol.

EXAMPLE 5

A solution of 2-(2-methylguanidino)-4-(4-phthalimidobutyl)thiazole hydrobromide (0.65 g.) in ethanol/water 3:1 v/v (50 ml.) containing sufficient sodium hydroxide to maintain the pH above 12 was heated under reflux for 15 minutes. The pH was then adjusted to 3 with concentrated hydrochloric acid and the solution heated under reflux for a further 15 minutes. The solution was then made strongly alkaline by addition of dilute sodium hydroxide and evaporated to dryness. The residue was dissolved in water (30 ml.) and the solution extracted with ethyl acetate (2×40 ml.). The combined ethyl acetate extracts were evaporated to dryness and the residue (0.27 g.) dissolved in ethanol (10 ml.) and treated with dimethyl (cyanoimido) dithiocarbonate (0.18 g.). The mixture was allowed to stand overnight to give a solution of 2-(2-methylguanidino)-4-[4-(3-cyano-2-methylisothioureido)butyl]thiazole in ethanol.

The 2-(2-methylguanidino)-4-(4-phthalimidobutyl)-thiazole hydrobromide used as starting material may be prepared as follows:

To a solution of (N-methylamidino)thiourea (0.4 g.) in hot ethanol (20 ml.) was added N-(6-bromo-5-oxohexyl)phthalimide (1.5 g.). The mixture was heated under reflux for 1 hour, cooled and evaporated to dryness. The residue was triturated with acetonitrile and the resulting solid was filtered and dried to give 2-(2-methylguanidino)-4-(4-phthalimidobutyl)thiazole hydrobromide, m.p. 210°–212° C.

EXAMPLE 6

To a solution of 2-(2-methylguanidino)-4-[4-(3-cyano-2-methylisothioureido)butyl]thiazole (0.38 g.) in ethanol (10 ml.) was added 33% w/v ethanolic methylamine (40 ml.). The mixture was stirred overnight, evaporated to dryness and the residue triturated with water. The solid thus obtained was filtered and dried to give 2-(2-methylguanidino)-4-[4-(2-cyano-3-methylguanidino)butyl]thiazole, m.p. 119°–122° C.

EXAMPLE 7

To a solution of 2-guanidino-4-(4-aminobutyl)-thiazole (0.8 g.) in ethanol (10 ml.) was added dimethyl (cyanoimido)dithiocarbonate (0.6 g.). The mixture was stirred overnight. The white precipitate was filtered off and recrystallized from acetonitrile to give 2-quanidino-4-[4-(3-cyano-2-methylisothioureido)butyl]thiazole, m.p. 178°–180° C.

EXAMPLE 8

A solution of 2-guanidino-4-[4-(3-cyano-2-methylisothioureido)butyl]thiazole (0.2 g.) in methanol (10 ml.) containing 0.005 g. sodium hydride (a 50% w/w dispersion in oil) was heated under reflux. After 4 hours the mixture was charcoal treated, filtered and evaporated to dryness. The residue was dissolved in acetone (10 ml.) and an excess of maleic acid in acetone added to precipitate the salt. This was filtered and dried to give 2-guanidino-4-[4-(3-cyano-2-methylisoureido)butyl]-thiazole hydrogen maleate, m.p. 174°–176° C.

EXAMPLE 9

2-Guanidino-4-[2-(2-cyano-3-(2-methoxyethyl)-guanidino)butyl]thiazole may be prepared by the following process:

A mixture of 2-methoxyethylamine (4 g.) and 2-guanidino-4-[4-(3-cyano-2-methylisothioureido)butyl]-thiazole (1 g.) in ethanol (15 ml.) is stirred at room temperature for three days. The mixture is evaporated to dryness and applied to Merck 60 F-254 preparative thin layer chromatography plates and eluted with chloroform/methanol/ammonia (s.g. 0.880) 5:1:0.1 v/v/v. The desired product may then be obtained by extraction of the appropriate region of the developed chromatograms with ethanol.

The above procedure using the appropriate amine in place of 2-methoxyethylamine may be used to prepare the following compounds:

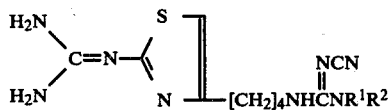

where
(i) $R^1=CH_2=CHCH_2$ and $R^2=H$ is made with the appropriate amount of allylamine in place of 2-methoxyethylamine;
(ii) $R^1=CH_3[CH_2]_5$ and $R^2=H$ is made with the appropriate amount of n-hexylamine in place of 2-methoxyethylamine;
(iii) $R^1=HOCH_2CH_2$ and $R^2=H$ is made with the appropriate amount of ethanolamine in place of 2-methoxyethylamine;
(iv) $R^1=Me_2NCH_2CH_2Al_2$ and $R^2=H$ is made with the appropriate amount of N-dimethylpropylamine in place of 2-methoxyethylamine; and
(v) $R^1$ and $R^2=-CH_3$ is made with the appropriate amount of dimethylamine in place of 2-methoxyethylamine.

EXAMPLE 10

2-Guanidino-4-[2-(2-cyano-3-cyclohexylguanidino)-butyl]thiazole may be prepared by the following process:

A mixture of cyclohexylamine (4 ml.), pyridine (6 ml.) and 2-guanidino-4-[4-(3-cyano-2-methylisothioureido)butyl]thiazole (1 g.) is allowed to stand at room temperature for two weeks. The mixture is evaporated and applied to Merck 60 F-254 preparative thin layer chromatography plates and eluted with chloroform/methanol/ammonia (s.g. 0.880) 5:1:0.1 v/v/v. The desired product may then be obtained by extraction of the appropriate region of the developed chromatograms with ethanol.

EXAMPLE 11

A mixture of 2-guanidino-4-(4-aminobutyl)thiazole (0.43 g.) and 1,1-di(methylthio)-2-nitroethylene (0.33 g.) in acetonitrile (15 ml.) was heated under reflux for 1 hour. The mixture evaporated to dryness and 33% w/v ethanolic methylamine (200 ml.) added. The mixture was stirred for 5 days at room temperature, then filtered and the filtrate evaporated to dryness. The residue was crystallized from ethanol to give 1-[4-(2-guanidino-thiazol-4-yl)butylamino]-1-methylamino-2-nitroethylene, m.p. 225° C. (decomposed).

EXAMPLE 12

A mixture of 2-guanidino-4-(4-aminobutyl)thiazole (0.43 g.) and 1,1-dicyano-2-methylamino-2-methylthio-ethylene (0.3 g.) in acetonitrile (10 ml.) was heated under reflux for 16 hours. The mixture was then evaporated to dryness and the resulting gum purified by chromatography on a silica column using chloroform/methanol/ammonia (s.g. 0.880) 80:20:0.5 v/v/v as developing solvent to give 1-[4-(2-guanidinothiazol-4-yl)butylamino]-1-methylamino-2,2-dicyanoethylene.

The n.m.r. spectrum of this product in $d_6$ dimethyl sulphoxide (DMSO) using tetramethylsilane as an internal standard ($\delta=0$) had the following resonances ($\delta$): 1.6 (4H, broad multiplet); 2.5 (obscured by DMSO); 2.8 (3H, doublet); 2.2 (obscured by $H_2O$); 6.25 (1H, singlet); 6.8 (4H, broad singlet); 7.2 (2H, broad multiplet).

EXAMPLE 13

2-Guanidino-4-[2-(2-methoxycarbonylguanidino)-butyl]thiazole may be prepared by the following process:

A mixture of 2-guanidino-4-(4-aminobutyl)thiazole hydrochloride hydrobromide (2.8 g.), triethylamine (2.1 g.) and 1-methoxycarbonyl-2-methylisothiourea (1.6 g.) in ethanol (25 ml.) is stirred at room temperature for 48 hours. The filtered solution is evaporated and the residue applied to Merck 60 F-254 preparative thin layer chromatography plates and eluted with chloroform/methanol/ammonia (s.g. 0.880) 5:1:0.1 v/v/v. The desired product may then be obtained by extraction of the appropriate region of the developed chromatograms with ethanol.

EXAMPLE 14

2-Guanidino-4-[2-(2-toluene-p-sulphonyl-3-methyl-guanidino)butyl]thiazole may be prepared by the following process:

A mixture of dimethyl(toluene-p-sulphonylimido)dithiocarbonate (0.90 g.), triethylamine (0.69 g.), 2-guanidino-4-(4-aminobutyl)thiazole hydrochloride hydrobromide (0.95 g.) and ethanol (10 ml.) is allowed to stand at room temperature for three days. An ethanolic solution of methylamine (33% w/v; 3 ml.) is added and the mixture allowed to stand at room temperature for three days. The mixture is evaporated to dryness and the residue applied to Merck 60 F-254 preparative thin layer chromatography plates and eluted with chloroform/methanol/ammonia (s.g. 0.880) 5:1:0.1 v/v/v. The desired product may then be obtained by extraction of the appropriate region of the developed chromatograms with ethanol.

EXAMPLE 15

A mixture of 2-guanidino-4-(4-aminobutyl)imidazole (0.15 g.) and methylisothiocyanate (0.1 g.) in ethanol (10 ml.) was stirred overnight and then evaporated to dryness. The residue was purified by chromatography on a silica gel column using chloroform/methanol/ammonia (s.g. 0.880) 80:20:0.3 v/v/v. The appropriate fractions on evaporation gave a gum which crystallized on triturating in petroleum ether (b.p. 40°-60° C.) to give 2-guanidino-4-[4-(3-methylthioureido)butyl]imidazole, m.p. 179°-184° C.

The 2-guanidino-4-(4-aminobutyl)imidazole used as starting material may be obtained as follows:

Biguanide (1.01 g.) was stirred in dry dimethylformamide (15 ml.) and N-(6-bromo-5-oxohexyl)phthalimide (1.5 g.) added. The mixture was stirred for 3 hours, acetic acid (5 ml.) was then added and the total reaction mixture evaporated to dryness. The residue was dissolved in water (10 ml.) and extracted with ethyl acetate (5×20 ml.). The combined ethyl acetate extracts were evaporated to give a brown foam which was purified by column chromatography on silica gel using chloroform/methanol/ammonia (s.g. 0.880) 80:20:0.5 v/v/v. The appropriate fractions were evaporated to give 2-guanidino-4-(4-phthalimidobutyl)imidazole as a brown foam (0.3 g.).

To a solution of 2-guanidino-4-(4-phthalimidobutyl)imidazole (0.25 g.) in water/ethanol 1:1 v/v (20 ml.) was added sufficient dilute sodium hydroxide solution to give a pH of 12. The mixture was heated under reflux for 30 minutes, the pH adjusted to 3 with concentrated hydrochloric acid, the mixture heated under reflux a further 30 minutes and then cooled. The pH was readjusted to 12 with sodium hydroxide solution and then the total mixture evaporated to dryness to give crude 2-guanidino-4-(4-aminobutyl)imidazole which was used without further purification.

EXAMPLE 16

A mixture of 2-guanidino-4-(6-aminohexyl)thiazole (1.0 g.; obtained from the dihydrochloride salt) and methyl isothiocyanate (0.45 g.) in ethanol (10 ml.) was stirred at room temperature for 16 hours and then evaporated to dryness. The residue was recrystallized from ethanol and the product dried over refluxing toluene for 2.5 hours to give 2-guanidino-4-[6-(3-methylthioureido)hexyl]thiazole, m.p. 162°-164° C.

The 2-guanidino-4-(6-aminohexyl)thiazole dihydrochloride used as starting material may be prepared as follows:

A mixture of phthalic anhydride (5.3 g.) and 7-aminoheptanoic acid (5.8 g.) was heated at 185°-190° C. for 40 minutes and then cooled. The cooled partially solidified product was dissolved in ethyl acetate and the solution washed several times with dilute HCl. The organic layer was dried (MgSO$_4$), filtered and evaporated to dryness and the residue recrystallized from acetic acid to give 7-phthalimidoheptanoic acid (5 g.), m.p. 112°-115° C.

A mixture of 7-phthalimidoheptanoic acid (5 g.) and thionyl chloride (4.3 g.) was stirred at room temperature for 2 hours. Toluene was added to the resulting solution and the mixture evaporated to dryness in vacuo. More toluene was added to the residue and the evaporation repeated. There was thus obtained the acid chloride (4.6 g.) as an oil which solidified on standing and was used without further purification.

To diazomethane (3 g.) in dry ether at −60° C. was added triethylamine (1.6 g.) followed by a solution of the above acid chloride (4.6 g.) in dry ether. The yellow solution rapidly became cloudy and was allowed to warm up to room temperature. The suspension was then filtered and the filtrate evaporated in vacuo at room temperature to a small volume and allowed to stand. The solid which crystallized out was filtered off, washed with a minimum amount of ether and dried to give the diazoketone (3.8 g.), m.p. 59°-61° C.

A solution of the above diazoketone (3.8 g.) in acetone (15 ml.) was treated dropwise with 48% w/v aqueous HBr at room temperature with stirring until no further gas evolution was noted. The solution was stirred at room temperature for a further 15 minutes then diluted with water (15 ml.) and the resulting precipitate filtered, washed with water and dried to give N-(8-bromo-7-oxooctyl)phthalimide (4.2 g.), m.p. 83°-86° C.

A mixture of amidinothiourea (1.4 g.) and ethanol (75 ml.) was heated to reflux and the suspension filtered to remove undissolved solids. The filtrate was reduced in volume to 25 ml. and this hot solution was added to a hot solution of N-(8-bromo-7-oxooctyl)phthalimide (4.2 g.) in ethanol (10 ml.). The mixture was heated under reflux for 45 minutes, evaporated to a small volume and allowed to stand at room temperature. The resulting solid precipitate was filtered off, washed with a minimum quantity of ethanol, then ether, and dried to give 2-guanidino-4-(6-phthalimidohexyl)thiazole hydrobromide (4.2 g.) which was used without further purification.

A suspension of 2-guanidino-4-(6-phthalimidohexyl)thiazole (4.2 g.) in methanol (30 ml.) and 10% w/v aqueous NaOH (10 ml.) was heated under reflux for 15 minutes. The pH of the mixture was then adjusted to 1 with concentrated HCl and the mixture heated under reflux for 30 minutes. The pH of the mixture was then adjusted to 12 with 10% w/v aqueous NaOH and the mixture heated under reflux for 15 minutes. The pH of the mixture was then adjusted to pH 1 with concentrated HCl and the mixture was heated under reflux for 30 minutes and then stirred at room temperature for 16 hours. The mixture was then evaporated to dryness in vacuo and the residue suspended in water and filtered to remove solids which were further washed with water. The combined aqueous filtrates were extracted several times with ethyl acetate, then with ether. The aqueous layer was evaporated to dryness and the residue extracted several times with ethanol. The combined ethanol extracts were evaporated to dryness, reextracted with ethanol and this extract filtered and evaporated to dryness to give 2-guanidino-4-(6-aminohexyl)thiazole dihydrochloride as a yellow foam which was used without further purification.

EXAMPLE 17

The process described in Example 1 was repeated using the equivalent amount of the appropriate amine in place of 2-guanidino-4-(4-aminobutyl)thiazole as starting material and the following compounds were thus obtained:

TABLE I $$\begin{array}{c}
\text{H}_2\text{N} \\
\phantom{XX}\diagdown \\
\phantom{XXXX}\text{C}=\text{N} \\
\phantom{XX}\diagup \\
\text{H}_2\text{N}
\end{array}
\quad
\begin{array}{c}
\text{S} \longrightarrow\!\!\!\!\!\!\begin{array}{c}\text{R}\\ \|\end{array} \\
\text{N} \longrightarrow (\text{CH}_2)_m\text{NHCNHCH}_3 \\
\phantom{XXXXXXXX}\|\\
\phantom{XXXXXXXX}\text{S}
\end{array}$$

| m | R | Footnotes |
|---|---|---|
| 2 | H | 1, 2, 3 |
| 3 | H | 4, 5, 6 |
| 4 | CH$_3$ | 1, 2, 5, 7 |
| 5 | H | 1, 4, 8, 9 |
| 5 | CH$_3$ | 1, 4, 9, 10 |

Footnotes
1. Free base of amine starting material prepared in situ from hydrohalide salt by addition of one equivalent of triethylamine.
2. Product purified by column chromatography on silica gel using chloroform/methanol/ammonia (s.g. 0.880) 8:2:0.4 v/v/v as solvent.
3. M.p. 184°–186° C.
4. Product purified by preparative thin layer chromatography on Merck 60 F-254 plates using chloroform/methanol/ammonia (s.g. 0.880) 7:3:0.5 v/v/v as solvent.
5. The product was characterized by its n.m.r. spectrum in d$_6$ dimethyl sulphoxide (DMSO) using tetramethylsilane as an internal standard ($\delta$=0).
6. N.m.r. spectrum ($\delta$): 1.8 (2H, broad triplet); 2.5 (triplet, obscured by DMSO); 2.8 (3H, doublet); 3.3 (multiplet, obscured by H$_2$O); 6.3 (1H, singlet); 6.9 (4H, broad singlet); 7.4 (2H, multiplet).
7. N.m.r. spectrum ($\delta$): 1.65 (4H, multiplet); 2.3 (3H, singlet); 2.6 (multiplet, obscured by DMSO); 3.0 (3H, doublet); 3.6 (multiplet, obscured by H$_2$O); 6.9 (4H, broad singlet); 7.5 (2H, multiplet).
8. N.m.r. spectrum ($\delta$): 1.5 $\delta$(6H, broad multiplet); 2.5 (2H, obscured by DMSO); 2.8 (3H, doublet); 3.3 (triplet, obscured by H$_2$O); 6.25 (1H, singlet); 6.8 (4H, broad singlet); 7.35 (2H, broad multiplet).
9. Product purified by preparative thin layer chromatography on Merck 60 F-254 plates using chloroform/methanol/ammonia (s.g. 0.880) 80:20:0.6 v/v/v as solvent.
10. N.m.r. spectrum ($\delta$) of sample containing 0.8 mole of ethanol: 1.1 (triplet, ethanol); 1.5 $\delta$(6H, multiplet); 2.1 $\delta$(3H, singlet); 2.4 (multiplet, obscured by DMSO and ethanol); 2.8 $\delta$(3H, doublet); 3.5 $\delta$(multiplet, obscured by H$_2$O); 6.7 (4H, broad singlet); 7.3 (2H, multiplet).

The starting materials for use in the above process may be obtained as follows:

A solution of 5-phthalimidopentanoyl chloride (1.8 g.) in dry toluene (30 ml.) was added to an ethereal solution of diazoethane at −78° C. and the mixture was allowed to warm to room temperature and stand for 15 hours. The solvent was evaporated off in vacuo, the residual oil dissolved in acetone, and to this solution was added concentrated hydrochloric acid until nitrogen ceased to be liberated. The mixture was then evaporated to dryness and azeotroped with toluene. Purification of the crude material by dry column chromatography on silica GF 254 and using 20% v/v ethyl acetate/toluene as solvent yielded N-(6-chloro-5-oxoheptyl)phthalimide (0.70 g.), m.p. 61°–63° C.

A solution of 6-phthalimidohexanoyl chloride (2 g.) in dry toluene was added to an ethereal solution of diazoethane at −78° C. and the mixture was allowed to warm to room temperature and stand for 15 hours. On standing a solid crystallized out of solution. The reaction mixture was filtered and the filtrate evaporated to dryness giving 1.43 g. of yellow-green oil. This oil was then dissolved in acetone and concentrated hydrochloric acid added until effervescence ceased. The resulting yellow-brown solution was then evaporated to dryness and azeotroped three times with toluene to give N-(7-chloro-6-oxooctyl)phthalimide (1.4 g.) which was used without further purification.

The second and third parts of Example 1 were then repeated using the appropriate starting materials in place of N-(6-bromo-5-oxohexyl)phthalimide and the compounds in the following Tables II and III were thus obtained:

TABLE II $$\begin{array}{c}
\text{H}_2\text{N} \\
\phantom{XX}\diagdown \\
\phantom{XXXX}\text{C}=\text{N} \\
\phantom{XX}\diagup \\
\text{H}_2\text{N}
\end{array}
\quad
\begin{array}{c}
\text{S} \longrightarrow\!\!\!\!\!\!\begin{array}{c}\text{R}\\ \|\end{array} \\
\text{N} \longrightarrow (\text{CH}_2)_m\!-\!\text{N}\!\!\begin{array}{c}\!\!\text{(phthalimide)}\end{array}
\end{array}\cdot \text{HX}$$

| m | R | X | m.p. °C. |
|---|---|---|---|
| 2 | H | Br | 285–287 |
| 3 | H | Br | 206–212 |
| 4 | CH$_3$ | Cl | 201–203 |
| 5 | H | Cl |  |
| 5 | CH$_3$ | Cl | * |

*In this instance and the product purified by preparative thin layer chromatography on Merck 60 F254 plates using chloroform/methanol/ammonia (s.g. 0.880) 8:2:0.3 v/v/v as developing solvent.

TABLE III $$\begin{array}{c}
\text{H}_2\text{N} \\
\phantom{XX}\diagdown \\
\phantom{XXXX}\text{C}=\text{N} \\
\phantom{XX}\diagup \\
\text{H}_2\text{N}
\end{array}
\quad
\begin{array}{c}
\text{S} \longrightarrow\!\!\!\!\!\!\begin{array}{c}\text{R}\\ \|\end{array} \\
\text{N} \longrightarrow (\text{CH}_2)_m\!-\!\text{NH}_2
\end{array}$$

| m | R | Footnotes |
|---|---|---|
| 2 | H | 1 |
| 3 | H | 2 |
| 4 | CH$_3$ | 3 |
| 5 | H | 3 |
| 5 | CH$_3$ | 3 |

Footnotes
1. Isolated as the hydrochloride hydrobromide salt.
2. The product was converted to the free base which was purified by preparative thin layer chromatography on Merck 60 F-254 plates using chloroform/methanol/ammonia (s.g. 0.880) 8:2:0.3 v/v/v as solvent.
3. Isolated as dihydrochloride salt.

EXAMPLE 18

To a solution of 2-guanidino-4-[5-(3-cyano-2-methylisothioureido)pentyl]thiazole in ethanol was added ethanolic methylamine (33% w/v, 15 ml.). The mixture was allowed to stand overnight and then evaporated to dryness. The residue was crystallized from acetonitrile to give 2-guanidino-4-[5-(2-cyano-3-methylguanidino)pentyl]thiazole, m.p. 109°–113° C.

The solution of 2-guanidino-4-[5-(3-cyano-2-methylisothioureido)pentyl]thiazole used as starting material may be prepared as follows:

To 2-guanidino-4-(5-aminopentyl)thiazole hydrochloride hydrobromide (1.2 g.) was added dilute aqueous sodium hydroxide solution (10 ml.). The mixture was stirred briefly, and the white precipitate (0.588 g.) filtered off. This material was dissolved in ethanol (10 ml.) and dimethyl (cyanoimido)dithiocarbonate (0.4 g.) added. The mixture was stirred 2.5 hours to give a solution of 2-guanidino-4-[5-(3-cyano-2-methylisothioureido)pentyl]thiazole.

EXAMPLE 19

To a stirred mixture of 2-guanidino-4-(4-aminobutyl)-5-methylthiazole dihydrochloride (0.56 g.) in ethanol (15 ml.) at room temperature was added triethylamine (0.52 ml.) and then dimethyl (cyanoimido)dithiocarbonate (0.25 g.) and the whole mixture stirred at room temperature for 15 hours. A solution of methylamine in ethanol (33% w/v; 20 ml.) was then added and the mixture stirred at room temperature for 5 hours. The mixture was evaporated to dryness and the residual gum was purified by column chromatography on silica gel using chloroform/methanol/ammonia (s.g. 0.880) 8:2:0.4 as solvent to give 2-guanidino-4-[4-(2-cyano-3-methylguanidino)butyl]-5-methylthiazole.

The product had the following n.m.r. spectrum in $d_6$ dimethyl sulphoxide using tetramethylsilane as an internal standard ($\delta=0$): 1.5 (4H, multiplet); 2.1 (3H, singlet); 2.4 (multiplet, obscured by DMSO); 2.6 (3H, doublet); 3.1 (2H, multiplet); 3.3 (singlet, $H_2O$); 6.8 (6H, multiplet).

EXAMPLE 20

To a mixture of 2-guanidino-4-(4-aminobutyl)thiazole hydrochloride hydrobromide (0.33 g.) in n-butanol (5 ml.) was added sodium dicyanimide (0.089 g.) and triethylamine (0.28 ml.). The whole mixture was heated under reflux for 2.5 hours, cooled to room temperature, filtered and the filtrate evaporated to dryness in vacuo. Preparative thin layer chromatography of the crude residue on Merck 60 F-254 plates using chloroform/methanol/ammonia (s.g. 0.880) 7:3:0.5 v/v/v as solvent gave 2-guanidino-4-[4-(2-cyanoguanidino)butyl]thiazole as an oil.

The product had the following n.m.r. spectrum in $d_6$ dimethyl sulphoxide using tetramethylsilane as an internal standard ($\delta=0$): 1.5 (4H, multiplet); 2.5 (multiplet, obscured by DMSO); 3.1 (2H, multiplet); 3.8 (broad singlet, $H_2O$); 6.4 (1H, singlet); 6.6 (2H, broad singlet); 7.0 (4H, multiplet).

EXAMPLE 21

To a solution of 2-guanidino-4-(4-aminobutyl)-thiazole (0.426 g.) in ethanol (10 ml.) was added 2-methyl-1-nitroisothiourea (0.270 g.). The mixture was heated under reflux for 4 hours, allowed to cool to room temperature, evaporated to dryness and the residue triturated with alcohol. The product was filtered off and dried to give 2-guanidino-4-[4-(2-nitroguanidino)butyl]-thiazole, m.p. 180°–181° C.

EXAMPLE 22

A mixture of 2-guanidino-4-(4-aminobutyl)thiazole (0.17 g.) and 1,2-dimethoxycyclobutene-3,4-dione (0.113 g.) in methanol (15 ml.) was stirred at ambient temperature for 6 hours. The product, 1-[4-(2-guanidinothiazol-4-yl)butylamino]-2-methoxycyclobutene-3,4-dione (0.05 g.) was filtered off and dried, m.p. 179°–180° C.

EXAMPLE 23

To a mixture of 1-[4-(2-guanidinothiazol-4-yl)butylamino]-2-methoxycyclobutene-3,4-dione (0.20 g.) in methanol (7 ml.) was added methylamine in ethanol (33% w/v; 7 ml.). The whole mixture was stirred at room temperature until a clear solution formed. The mixture was evaporated to dryness, and the residue triturated with methanol, the product, 1-[4-(2-guanidinothiazol-4-yl)butylamino]-2-methylaminocyclobutene-3,4-dione was filtered off and dried, m.p. 184°–186° C.

EXAMPLE 24

A mixture of 2-guanidino-4-(4-aminobutyl)-5-bromothiazole (0.50 g.) and methylisothiocyanate (0.14 g.) in ethanol (20 ml.) was stirred for 1 hour at room temperature. The mixture was evaporated to dryness, and residual gum was purified by preparative thin layer chromatography on Merck 60 F-254 plates using chloroform/methanol/ammonia (s.g. 0.880) 8:2:0.2 v/v/v as solvent to give 2-guanidino-5-bromo-4-[4-(2-methylthioureido)butyl]thiazole, m.p. 128°–131° C.

The 2-guanidino-4-(4-aminobutyl)-5-bromothiazole used as starting material may be prepared as follows:

A mixture of 2-guanidino-4-(4-aminobutyl)thiazole (0.5 g.) and 10% v/v bromine in concentrated hydrochloric acid (1.5 ml.) in concentrated hydrochloric acid (10 ml.) was stirred at room temperature for 0.75 hours. The whole mixture was evaporated to dryness and azeotroped twice with toluene. The residue was dissolved in water (5 ml.) and excess 3 N sodium hydroxide added quickly with stirring. The product, 2-guanidino-4-(4-aminobutyl)-5-bromothiazole (0.5 g.) was filtered off, washed with a little water, and dried, m.p. 125°–126° C.

EXAMPLE 25

2-(2-Acetylguanidino)-4-[(2-cyano-3-methylguanidino)butyl]thiazole may be prepared by the following process:

Acetic anhydride (0.40 g.) is added to a stirred suspension of 2-guanidino-4-[(2-cyano-3-methylguanidino)butyl]thiazole (1.0 g.) in pyridine (6 ml.) at room temperature. After stirring for two hours the mixture is diluted with water (50 ml.), extracted with methylene chloride (3×30 ml.) and the combined extracts washed with water (100 ml.), dried (magnesium sulphate) and evaporated. The residue is applied to Merck 60 F-254 preparative thin layer chromatography plates and eluted with chloroform/methanol/ammonia (s.g. 0.880) 5:1:0.1 v/v/v. The desired product may be obtained by extraction of the appropriate region of the developed chromatograms with ethanol.

In a similar manner, the above reaction with propionic anhydride may be carried out to give 2-(3-propionylguanidino)-4-[(2-cyano-3-methylguanidino)butyl]thiazole.

EXAMPLE 26

2-(2-Benzoylguanidino)-4-[(2-cyano-3-methylguanidino)butyl]thiazole may be prepared by the following process:

A solution of benzoic anhydride (0.73 g.) in pyridine (5 ml.) is added to a stirred suspension of 2-guanidino-4-[(2-cyano-3-methylguanidino)butyl]thiazole (1.0 g.) in pyridine (5 ml.). The mixture is stirred for 24 hours, diluted with water (50 ml.) and the precipitate collected to give 2-(2-benzoylguanidino)-4-[(2-cyano-3-methylguanidino)butyl]thiazole.

EXAMPLE 27

A solution of 2-guanidino-4-(3-aminoprop-1-trans-enyl)thiazole (0.066 g.) in ethanol at 40° C. was treated with dimethyl (cyanoimido)dithiocarbonate (0.038 g.) and the solution kept at room temperature for 1 hour. The pale yellow solid which crystallized from the solution was collected to give 2-guanidino-4-[3-(3-cyano-2-methylisothioureido)prop-1-trans-enyl]thiazole, m.p. 223°–225° C. (decomposed).

The 2-guanidino-4-(3-aminoprop-1-trans-enyl)-thiazole used as starting material may be prepared as follows:

A solution of (3-chloroacetonylidene)triphenylphosphine (3.0 g.) and 2-phthalimidoacetaldehyde (1.62 g.) in chloroform (50 ml.) was heated under reflux for 48 hours, then evaporated to dryness under reduced pressure. The residue was crystallized from ethanol to give N-(5-chloro-4-oxopent-2-trans-enyl)phthalimide (1.29 g.), m.p. 124°–126° C.

A mixture of N-(5-chloro-4-oxopent-2-trans-enyl)phthalimide (b 1.29 g.), amidinothiourea (0.59 g.) and ethanol (20 ml.) was heated under reflux for one hour. The resulting solution was cooled, then filtered to give 2-guanidino-4-(3-phthalimidoprop-1-trans-enyl)thiazole hydrochloride (0.97 g.), m.p. 238°–240° C. (decomposed).

A mixture of 2-guanidino-4-(3-phthalimidoprop-1-trans-enyl)thiazole hydrochloride (0.97 g.), hydrazine hydrate (0.27 g.) and methanol (20 ml.) was heated under reflux for 2 hours then evaporated to dryness. The solid residue was stirred for 5 minutes with 2 N HCl (20 ml.) then filtered, and the filtrate evaporated to dryness. The residue was dissolved in water (10 ml.) and the solution adjusted to pH 12 with 2 N NaOH, saturated with sodium chloride and extracted five times with ethyl acetate. The combined ethyl acetate extracts were dried and evaporated to dryness to give 2-guanidino-4-(3-aminoprop-1-trans-enyl)thiazole (0.35 g.), characterized as the dihydrochloride, m.p. 249°–251° C. (after crystallization from aqueous ethanol).

EXAMPLE 28

A mixture of 2-guanidino-4-[3-(3-cyano-2-methylisothioureido)prop-1-trans-enyl]thiazole (0.11 g.) and 33% w/v ethanolic methylamine (2 ml.) was stirred at room temperature for 2 hours, then the solution evaporated to dryness. The residue was crystallized from a mixture of methanol and acetonitrile to give 2-guanidino-4-[3-(2-cyano-3-methylguanidino)prop-1-trans-enyl)]thiazole, m.p. 213°–216° C. (decomposed).

EXAMPLE 29

A mixture of 2-guanidino-4-(4-phthalimidobut-1-trans-enyl)thiazole hydrochloride (0.5 g.), hydrazine hydrate (0.2 g.) and methanol (15 ml.) was heated under reflux for 1.5 hours. The solution was cooled, treated with N,N,N',N'-tetramethylguanidine (0.3 g.), and evaporated to dryness, then the residue twice suspended in toluene (20 ml.) and evaporated to dryness.

A solution of the residue in ethanol (10 ml.) at 40° C. was treated with dimethyl (cyanoimido)dithiocarbonate (0.175 g.) and the solution kept at room temperature for 2 hours then evaporated to dryness. The residue was stirred with water (10 ml.) for 5 minutes, then the aqueous phase decanted and the residue washed with a further 10 ml. of water.

The residue was dissolved in 33% w/v methylamine in ethanol (5 ml.) and the solution kept at room temperature for 4 hours then evaporated to dryness. The residue was purified by preparative thin layer chromatography on Merck 60 F-254 plates using ethyl acetate/ethanol/ammonia (s.g. 0.880) 12:1:1 v/v/v as solvent and the band having $R_f$ 0.3 was eluted with methanol to give 2-guanidino-4-[4-(2-cyano-3-methylguanidino)but-1-trans-enyl]thiazole (0.08 g.), characterized as its hydrogen maleate, m.p. 163°–165° C. (decomposed) (after crystallization from methanol/acetonitrile).

The 2-guanidino-4-(4-phthalimidobut-1-trans-enyl)thiazole hydrochloride used as starting material may be obtained as follows:

A solution of (3-chloroacetonylidine)triphenylphosphine (8.68 g.) and 3-phthalimidopropionaldehyde (5 g.) in chloroform (80 ml.) was heated under reflux for 24 hours. The solution was evaporated to dryness and the residue triturated with ethanol then filtered to give N-(6-chloro-5-oxohex-3-trans-enyl)phthalimide (3.4 g.), m.p. 132°–135° C. (after recrystallization from ethanol).

A mixture of N-(6-chloro-5-oxohex-3-trans-enyl)phthalimide (0.554 g.), amidinothiourea (0.236 g.) and ethanol (30 ml.) was heated under reflux for 3.5 hours. The mixture was allowed to cool, then filtered to give 2-guanidino-4-(4-phthalimidobut-1-trans-enyl)thiazole hydrochloride, m.p. 226° C. (decomposed).

As noted above, the guanidine derivatives of the invention are a histamine H-2 antagonist, inhibit the secretion of gastric acid in warm-blooded animals and are therefore useful in the treatment of peptic ulcers and other conditions caused or exacerbated by gastric acidity, such as stress ulceration or gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig heart or by its ability to inhibit the histamine-induced increase in the level of cyclic AMP (3,5-adenosine monophosphate), in the presence of a phosphodiesterase inhibitor, in a free cell suspension obtained from canine gastric mucosa.

The guinea pig heart atrium test is carried out as follows:

A guinea pig right atrium is suspended at 1 g. tension (isometric) in a thermostatically controlled (30° C.) tissue bath (25 ml.) containing oxygenated (95% $O_2$; 5% $CO_2$) Krebs-Hanseleit buffer (pH 7.4). The tissue is allowed to stabilize over 1 hour during which time it is washed 2–4 times. Individual contractions are recorded with a force-displacement transducer through a strain gauge coupler, and instantaneous rates are monitored with a cardiotachometer. A control response to 1 micromole histamine in the above described tissue bath is obtained after which the tissue is washed 3 times and allowed to re-equilibrate to basal rate. After re-equilibration for 15 minutes, the test compound is added to the tissue bath at the desired final concentration. Ten minutes after addition of the compound, a fresh histamine (1 micromole) bath solution is again added to the tissue bath containing the test compound. Then the response to histamine in the presence of antagonist is compared to the histamine control response. The result is expressed as a percentage of the histamine control response. Thereafter, the apparent dissociation constant of the H-2 antagonist is determined by standard procedures.

All the compounds exemplified in this specification are active on the guinea pig heart atrium test at or below a bath concentration of 10 micromoles, and the more active compounds show complete inhibition of response at this concentration.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, cats or dogs provided with gastric fistulae and whose gastric secretion is stimulated by the administration of a secretagogue, for example pentagastrin or histamine.

The test in dogs in carried out as follows:

A female pure bred beagle (9–12 kg.) having a chronic gastric fistula is fasted overnight with water ad lib. During the experiment the dog is lightly restrained in a standing position. When studying the test compound by the intravenous route, the fistula is opened and, after ascertaining the absence of secretion over a period of 30 minutes, a continuous intravenous infusion of secretagogue (0.5 micromole/kg./hour of histamine or 2 micrograms/kg./hour pentagastrin) in saline (15 ml./hour) is begun. Gastric acid samples are collected every 15 minutes. The volume of each sample is measured and a 1 ml. aliquot is titrated to neutrality with 0.1 N NaOH to determine acid concentration. When a plateau of secretion is reached (1-2 hours), the test compound is administered intravenously in saline and gastric acid samples are collected for a further 2-3 hours during which time the infusion of secretagogue continues uninterrupted.

When studying the test compound by the intragastric route, the absence of secretion over a period of 30 minutes is ascertained and the test compound, contained in 25 ml. of 0.5% w/v hydroxypropyl methylcellulose and 0.1% w/v TWEEN 80 polyoxyethylene(20) sorbitan monooleate in water (TWEEN is a trademark of ICI Americas Inc.), is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

In all but one case the results obtained in the heart atrium test are predictive of activity in the dog test.

No overt toxicity or side effects were noted with any of the compounds during the dog tests. The following compounds, chosen at random from among the compounds exemplified in this specification, showed no overt toxicity when dosed intraperitoneally to groups of 4 or 5 mice at the dose indicated.

$$R^2NH-C(=N-)(NH_2)-\text{thiazole}-CH_2-Y-(CH_2)_n-NHC(=Z)NHR^5$$

| n | Y | Z | $R^2$ | $R^5$ | Dose (mg./kg.) |
|---|---|---|---|---|---|
| 3 | $CH_2$ | S | H | $CH_3$ | 100 |
| 3 | $CH_2$ | NCN | $CH_3$ | $CH_3$ | 100 |

According to a further feature of the invention there is provided a pharmaceutical composition which comprises a guanidine derivative of the invention in association with a non-toxic pharmaceutically acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the guanidine derivatives of formula I, the pharmaceutical composition of the invention for oral, rectal or parenteral administration may also contain, or be co-administered with, one or more known drugs selected from antacids, for example aluminum hydroxide-magnesium hydroxide mixtures; antipepsin compounds, for example pepstatin; other histamine H-2 antagonists, for example cimetidine; ulcer healing agents, for example dihydrocanadensolide, carbenoxolone or bismuth salts; anti-inflammatory agents, for example ibuprofen, indomethacin, naproxen or aspirin; prostaglandins, for example 16,16-dimethyl-prostaglandin $E_2$; classical antihistamines (histamine H-1 antagonists), for example pyrilamine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical antihistamines (histamine H-1 antagonists), for example pyrilamine or diphenhydramine and/or one or more steroidal anti-inflammatory agents, for example fluocinolone or triamcinolone. A topical formulation may contain 1-10% w/w of the guanidine derivative of the invention.

A preferred pharmaceutical composition of the invention is one suitable for oral administration in unit dosage form, for example a tablet or capsule which contains between 10 mg. and 500 mg. of the guanidine derivative, or one suitable for intravenous, subcutaneous or intramuscular injection, for example a sterile aqueous solution containing between 0.1% and 10% w/w of the guanidine derivative.

Examples of formulations for preparing tablets, capsules, liquids, parenterals, and suppositories containing the guanidine derivatives of the present invention are described below. It will be recognized by one skilled in the present art that other known methods of preparing such pharmaceutical compositions can be used and obviously the size of the tablet or capsule or the strength of the dosage form may be suitably varied in order to satisfy the particular requirements, such as dosage level indicated. Any of the well-known suitable pharmaceutical carriers can be used to prepare acceptable dosage forms so as to provide an effective amount or therapeutically effective amount of the compound to be administered.

| Tablet Containing 50 mg. of 2-guanidino-4-[4-(2-cyano-3-methylguanidino)butyl]thiazole hydrochloride | 1000 Tablets (Grams) |
|---|---|
| 2-guanidino-4-[4-(2-cyano-3-methylguanidino)-butyl]thiazole hydrochloride | 50 |
| Starch | 102 |
| Powdered Lactose | 102 |
| Talc | 26 |
| Weight of Granulation | 280 |

Combine all ingredients, mix, and then compress into slugs. The slugs should then be ground to form granules that will pass through a 14 to 16 mesh screen. The granules may then be recompressed into tablets using a suitable compression mold to form tablets, each weighing 280 mg.

| Capsule Containing 100 mg. of 2-(2-methylguanidino)-4-[4-(2-cyano-3-methylguanidino)butyl]thiazole | |
|---|---|
| 2-(2-methylguanidino)-4-[4-(2-cyano-3-methylguanidino)butyl]thiazole | 100 mg. |
| Powdered Lactose | 200 mg. |
| D.T.D. Capsules No. 1000 | |

Mix the ingredients so as to evenly distribute the active ingredient throughout the lactose. Pack the powder into a No. 1 empty gelatin capsule.

| Suspension Containing 50 mg. per 5 cc. of 1-[4-(2-guanidinothiazol-4-yl)butylamino]-1-methylaino-2-nitroethylene | |
|---|---|
| 1-[4-(2-guanidinothiazol-4-yl)butylamino]-1-methylamino-2-nitroethylene | 10 grams |
| Tragacanth | 50 grams |
| Amaranth | 10 grams |
| Syrup Wild Cherry | 60 ml. |
| Distilled Water q.s. | 1000 ml. |

Hydrate the tragacanth with sufficient water to form a smooth paste and to this add the 1-[4-(2-guanidinothiazol-4-yl)butylamino]-methylamino-2-nitroethylene, followed by the amaranth which has been previously dissolved in water. Then add the syrup of wild cherry and add distilled water to make 1000 ml.

| Injectable Containing 5 mg of 2-guanidino-4-[4-(2-nitroguanidino)butyl]thiazole hydrochloride Per Milliliter | |
|---|---|
| 2-guanidino-4-[4-(2-nitroguanidino)butyl]thiazole hydrochloride | 5.0 grams |
| Chlorobutanol | 3.0 grams |
| Propylene Glycol | 20.0 ml. |
| Water for Injectin q.s. | 1000.0 ml. |

Combine the above ingredients, clarify by filtration, fill into vials, seal, and sterilize.

| Suppository Containing 200 mg. of 1-[4-(2-guanidinothiazol-4-yl)butylamino]-2-methylaminocyclobutene-3,4-dione | |
|---|---|
| 1-[4-(2-guanidinothiazol-4-yl)butylamino]-2-methylaminocyclobutene-3,4-dione | 0.2 gram |
| Cocoa Butter | 1.8 grams |
| Make of Such No. 100 | |

Melt cocoa butter and disperse the 1-[4-(2-guanidinothiazol-4-yl)butylamino]-2-methylaminocyclobutene-3,4-dione in the molten mass and stirr until uniform. Pour the resulting molten mass into suppository mold and chill. Remove suppositories from mold and package.

| Cream Containing 5% w/w of 2-guanidino-4-[4-(3-cyano-2-methylisoureido)butyl]thiazole phosphate | |
|---|---|
| 2-guanidino-4-[4-(3-cyano-2-methylisoureido)butyl]thiazole phosphate | 5 grams |
| Cold Cream | 95 grams |

Disperse 2-guanidino-4-[4-(3-cyano-2-methylisoureido)butyl]thiazole phosphate in 5 ml. water and blend into the cold cream. Grind the resulting mixture to obtain a uniform and smooth product.

Evaluation in laboratory animals indicates that the present guanidine derivatives or compounds can be used to inhibit the secretion of gastric acid when administered in a therapeutically effective amount to a living, warm-blooded animal in need of treatment for peptic ulcers and other conditions caused or exacerbated by gastric acidity. The effectiveness and dosage required vary, as is customary in this art, with the species being treated, particular disorder being treated, weight of the animal, and the route of administration. In accordance with the present invention, the subject compounds can be used in living animals, for example dogs, in need of such treatment at doses from about 0.03 milligram to 30 milligrams per kilogram body weight (for example b 3 mg./kg.) as needed, generally 2 to 4 times a day. A more preferred dose, in view of optimum results and low dosage, is from about 0.3 milligram to 3 milligrams per kilogram body weight (for example 1 mg./kg.) as needed, generally 2 to 4 times a day.

The compounds or pharmaceutical composition of the invention will normally be administered to humans for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus each human patient will receive an oral dose of between 15 mg. and 1500 mg. and preferably between 20 mg. and 200 mg. of a guanidine derivative of the present invention (for example, 50 mg. orally for an adult human) or an intravenous, subcutaneous or intramuscular dose of between 1.5 mg. and 150 mg., and preferably between 5 mg. and 20 mg. of a guanidine derivative of the present invention, the subject guanidine derivative being administered 2 to 4 times per day. The rectal dose will be approximately the same as the oral dose. The composition may be administered less frequently when it contains an amount of guanidine derivative which is a multiple of the amount which is effective when given 2-4 times per day.

What we claim is:

1. A guanidine derivative of the formula:

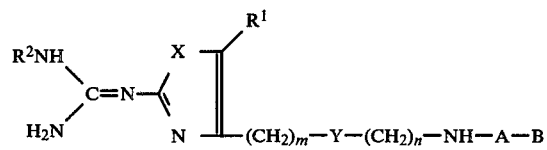

in which X is a sulphur atom or NH radical; Y is a direct bond, a methylene radical or a cis- or trans-vinylene radical; m is 0 to 4 and n is 1 to 4; $R^1$ is a hydrogen or halogen atom or an alkyl radical of 1 to 6 carbon atoms; $R^2$ is a hydrogen atom, an alkyl radical of 1 to 10 carbon atoms, an alkanoyl radical of 1 to 6 carbon atoms or an aroyl radical of 7 to 11 carbon atoms; A is a 3,4-dioxocyclobuten-1,2-diyl radical or a radical of the formula C=Z in which Z is an oxygen or sulphur atom or a radical of the formula NCN, NNO$_2$, CHNO$_2$, NCONH$_2$, C(CN)$_2$, NCOR$^3$, NCO$_2$R$^3$, NSO$_2$R$^3$ or NR$^4$ in which $R^3$ is an alkyl radical of 1 to 6 carbon atoms or an aryl radical of 6 to 12 carbon atoms and $R^4$ is a hydrogen atom or an alkyl radical of 1 to 6 carbon atoms; B is an alkoxy or alkylthio radical of 1 to 6 carbon atoms or a radical of the formula NR$^5$R$^6$ in which $R^5$ and $R^6$, which may be the same or different, are hydrogen atoms, alkyl radicals of 1 to 10 carbon atoms, alkenyl radicals of 3 to 10 carbon atoms in which the double bond is separated from the nitrogen atom of $NR^5R^6$ by at least one carbon atom, cycloalkyl radicals of 3 to 8 carbon atoms, (primary hydroxy)alkyl radicals of 2 to 6 carbon atoms in which the oxygen atom is separated from the nitrogen atom of $NR^5R^6$ by at least two carbon atoms, alkoxyalkyl radicals of 3 to 10 carbon atoms in which the oxygen atom is separated from the nitrogen atom of $NR^5R^6$ by at least two carbon atoms, alkylaminoalkyl radicals of 3 to 10 carbon atoms in which the nitrogen atom is separated from the nitrogen atom of $NR^5R^6$ by at least two carbon atoms; or dialkylaminoalkyl radicals of 4 to 10 carbon atoms in which the nitrogen atom is separated from the nitrogen atom of $NR^5R^6$ by at least two carbon atoms; and the pharmaceutically acceptable acid-addition salts thereof.

2. A compound of claim 1 wherein X is a sulphur atom or an NH radical; Y is a direct bond or a methylene radical; m is 1 to 4 and n is 1 to 4; $R^1$ is a hydrogen or bromine atom or methyl radical; $R^2$ is a hydrogen atom, or a methyl, n-butyl, acetyl, propionyl or benzoyl radical; A is a 3,4-dioxocyclobuten-1,2-diyl radical or a radical of the formula C=Z in which Z is an oxygen or sulphur atom or a radical of the formula NCN, $NNO_2$, $CHNO_2$, $NCONH_2$, $C(CN)_2$, $NCO_2CH_3$, $NSO_2$-p-tolyl or $NCH_3$; B is a methoxy, ethoxy or methylthio radical or a radical of the formula $NR^5R^6$ in which $R^5$ and $R^6$ are independently selected from the group consisting of methyl, ethyl, n-propyl, isopropyl, n-hexyl, allyl, cyclohexyl, 2-hydroxyethyl, 3-hydroxypropyl, 2-methoxyethyl and 2-dimethylaminoethyl radicals.

3. A compound of claim 1 wherein X is a sulphur atom.

4. A compound of claim 3 wherein Y is a methylene radical.

5. A compound of claim 4 wherein $R^1$ is a hydrogen atom.

6. A compound of claim 5 where $R^2$ is a hydrogen atom.

7. A compound of claim 6 where A is C=Z wherein Z is NCN.

8. A compound of claim 7 where B is $NR^5R^6$ wherein $R^5$ is methyl and $R^6$ is methyl.

9. A compound of claim 1 where X is a sulphur atom; Y is a methylene radical; m is 1 to 4; n is 1 to 4; $R^1$ is a hydrogen atom; $R^2$ is a hydrogen atom or a methyl radical; A is C=Z wherein Z is a sulphur atom or a radical of the formula NCN, $NNO_2$, $NCONH_2$, $NCOR^3$, $NCO_2R^3$ or $NSO_2R^3$ in which $R^3$ is a phenyl radical; and B is a radical of the formula $NR^4R^5$ wherein $R^4$ and $R^5$ are independently selected from the group consisting of hydrogen and lower alkyl radicals of 1 to 4 carbon atoms.

10. A compound of claim 1 where X is a sulphur atom; Y is a methylene radical; m is 1 to 4; n is 1 to 4; $R^1$ is hydrogen; $R^2$ is hydrogen; A is C=Z where Z is a sulphur atom or a radical of the formula NCN; and B is a radical of the formula $NR^4R^5$ wherein $R^4$ and $R^5$ are independently selected from the group consisting of hydrogen and lower alkyl radicals of 1 to 4 carbon atoms.

11. A compound of claim 4 where m is 1 and n is 1 or 2.

12. A compound of claim 1 which is 2-guanidino-4-[4-(2-cyano-3-methylguanidino)butyl]thiazole.

13. A compound of claim 1 which is 2-(2-methylguanidino)-4-[4-(2-cyano-3-methylguanidino)butyl]thiazole.

14. A compound of claim 1 which is 2-guanidino-4-[4-(3-cyano-2-methylisoureido)butyl]thiazole.

15. A compound of claim 1 which is 1-[4-(2-guanidinothiazol-4-yl)butylamino]-1-methylamino-2-nitroethylene.

16. A compound of claim 1 which is 2-guanidino-4-[4-(2-nitroguanidino)butyl]thiazole.

17. A compound of claim 1 which is 1-[4-(2-guanidinothiazol-4-yl)butylamino]-2-methylaminocyclobutene-3,4-dione.

18. A pharmaceutical composition to inhibit gastric acid secretion comprising a therapeutically effective amount of a compound of claim 1 to inhibit said secretion in a pharmaceutical carrier.

19. A pharmaceutical composition to inhibit gastric acid secretion comprising a therapeutically effective amount of a compound of claim 13 to inhibit said secretion in a pharmaceutical carrier.

20. A method of inhibiting gastric acid secretion in a living animal comprising administering to the animal a composition of claim 18.

* * * * *

UNITED STATES PATENT AND TRADEMARK OFFICE
CERTIFICATE OF CORRECTION

PATENT NO. : 4,165,377
DATED : August 21, 1979
INVENTOR(S) : Derrick F. Jones & Tobias O. Yellin It is certified that error appears in the above-identified patent and that said Letters Patent are hereby corrected as shown below:

[73] "Assignee: " ICI Americas Inc., Wilmington, Delaware" should read --Assignees: Imperial Chemical Industries Limited, Millbank, London, England and ICI Americas Inc., Wilmington, Delaware--.

Col. 21, line 51, right end of structural formula

"$-NHCNH^5$" should read -- $-NHCNHR^5$ --.

Col. 23, line 26 - "1-[4-(2-guanidinothiazol-4-yl)butylamino]-methylamino-2-nitroethylene" should read --1-[4-(2-guanidinothiazol-4-yl)butylamino]-1-methylamino-2-nitroethylene--.

Col. 24, line 14 - "milligrams per kilogram body weight (for example b3" should read --milligrams per kilogram body weight (for example 3--.

Signed and Sealed this

Fifteenth Day of January 1980

[SEAL]

Attest:

SIDNEY A. DIAMOND

Attesting Officer     Commissioner of Patents and Trademarks